United States Patent [19]

Butler et al.

[11] Patent Number: 5,606,969
[45] Date of Patent: Mar. 4, 1997

[54] METHODS FOR MEASURING LUNG FUNCTION USING DIFFUSED LIGHT

[75] Inventors: James P. Butler, Brookline; George P. Topulos, Dedham; John L. Lehr, Newton, all of Mass.

[73] Assignees: Brigham & Women'Hospital, Boston; The President and Fellows of Harvard College, Cambridge, both of Mass.

[21] Appl. No.: 414,416

[22] Filed: Mar. 31, 1995

[51] Int. Cl.⁶ .................................................. A61B 5/00
[52] U.S. Cl. ...................... 128/653.1; 128/633; 128/634; 128/664; 128/665
[58] Field of Search .............................. 128/653.1, 664, 128/665, 633, 634; 600/178–183

[56] References Cited

U.S. PATENT DOCUMENTS

| | | |
|---|---|---|
| 3,910,701 | 10/1975 | Henderson et al. . |
| 5,054,487 | 10/1991 | Clarke . |
| 5,190,039 | 3/1993 | Takeuchi et al. . |
| 5,441,053 | 8/1995 | Lodder et al. . |
| 5,528,365 | 6/1996 | Gonatas . |

OTHER PUBLICATIONS

1953 Morse et al., *Methods of Theoretical Physics, Part I.*, New York: McGraw–Hill.
1955 Mead et al., *J.C.I.* 34:1005–1016.
1968 Kress et al., *Diseases of the Chest* 53:427–435.
1970 van Assendelft, *Spectrophotometry of Haemoglobin Derivatives*, Charles C. Thomas, Assen, The Netherlands.
1970 Forrest, *J. Physiol. London* 210:533–547.
1970 Klingele et al., *J. Appl. Physiol.* 28:411–414.
1970 Mead et al., *J. Appl. Physiol.* 28:596–608.
1972 Gil et al., *Respir. Physiol.* 15:190–213.
1975 Fung, *Circ. Res.* 37:481–496.
1979 Weibel, Stereological Methods vol. 1, *Practical Methods for Biological Morphometry*, Chapter 2, London: Academic Press.
1979 Gil et al., *J. Appl. Physiol.* 47:990–1001.
1979 Bachofen et al., *J. Appl. Physiol.* 47:1002–1010.
1980 Karakaplan et al., *J. Biomech. Eng.* 102:124–136.
1981 Wilson, *J. Appl. Physiol.* 50:921–926.
1985 Lehr et al., *J. Appl. Physiol.: Respirat. Environ. Exercise Physiol.* 59:623–633.
1985 Butler et al., *J. Appl. Physiol.* 58:89–96.
1985 Suzuki et al., *J. Appl. Physiol.* 58:97–104.
1989 Butler et al., *J. Appl. Physiol.* 67:1873–1880.
1991 Chance, *Annu. Rev. Biophys. Biophys. Chem.* 20:1–28.
1993 Miki et al., *J. Appl. Physiol.* 75:1630–1636.
1994 *American Lung Association Lung Disease Data*, Publication of American Lung Association.
1995 Cooper et al., *J. Thoracic & Cardiovas. Surg.* 109:106–119.

Primary Examiner—Marvin M. Lateef
Assistant Examiner—Shawna J. Shaw
Attorney, Agent, or Firm—Bromberg & Sunstein

[57] ABSTRACT

The method and device of the invention provides a measure of lung function at a preselected region of the lung by detecting and measuring light scattering following contact of the light onto lung tissue. Multiple parameters concerning the status of the lungs can be measured using a variety of wavelengths of light targeted at the lung tissue. In this way it is possible to determine regions of impaired lung function in patients with emphysema. The device utilizes an optical fiber, a light collection system and a spectral separation device to provide an image of the lung and to determine functional parameters such as gas exchange.

21 Claims, 7 Drawing Sheets

METHODS FOR MEASURING LUNG FUNCTION USING DIFFUSED LIGHT

FUNDING

Work described herein was supported by funding from the National Institute of Health. The United States Government has certain rights in the invention.

TECHNICAL FIELD

The present invention relates to methods and devices for measuring lung structure and function in a living animal over preselected regions of the lung.

BACKGROUND OF THE INVENTION

The lung is an organ dedicated to gas exchange. Gas exchange occurs at the septal surface of the approximately 300 million alveoli in the adult human lung. These myriads of units provide a large diffusion area (50–100 square meters for a human lung) where gas exchange occurs between the air entering the alveoli and the blood contained in capillaries wrapped around the alveoli.

Classic concepts of the mechanics and functioning of the lung at the level of alveoli and alveolar ducts have relied on inferences largely drawn from three different sources. These sources are:

1) Determining airway pressure and volume ventilation to obtain mechanical structure-function information on the whole lung, which in turn reflects on the properties of the lung's connective tissue and the mean properties of the air-liquid surfaces;

2) In vitro analyses of biopsies taken from a small number of regions of the lung to determine the presence of infection or tumor tissue; and 3) Visual methods including computer aided tomography and X-rays which may be used to identify gross morphological changes in vivo such as blockages, lumps and inflammation but are not suited for fine resolution imaging because of interference caused by the gas-liquid interfaces in the lungs.

4) Morphometric analysis of lung tissue fixed and sectioned for microscopy.

5) Gas exchange analyses of gross and large regional differences by multiple inert gas exchange, positron emission tomography and single photon emission tomography.

None of these methods provide direct means for measuring the dynamic properties of large numbers of small regions within the lungs of a living animal in real time.

Recent advances have brought about the recognition that the relevant structural geometry (Fung,(1975), Stress, deformation, and atelectasis of the lung, *Circ. Res.* 37:481–496; Karakaplan et al., (1980), A mathematical model of lung parenchyma, *J. Biomech. Eng.* 102:124–136; Mead et al., (1970) Stress distribution in lungs: a model of pulmonary elasticity, *J. Appl. Physiol.* 28:596–608; Wilson,(1981) Relations among recoil pressure, surface area, and surface tension in the lung, *J. Appl. Physiol.* 50:921–926) of the lung is highly complex. Stereological techniques have been used on fixed tissues for measuring the effects on the alveolar surface configuration of changes in lung volume (Forrest, (1970), The effect of changes in lung volume on the size and shape of alveoli, *J. Physiol. London* 210:533–547; Gil et al., Morphological study of pressure-volume hysteresis in rat lungs fixed by vascular perfusion, *Respir. Physiol.* 15:190–213 (1972); Gil et al., Alveolar volume-surface area relation in air-and saline-filled lungs fixed by vascular perfusion, *J. Appl. Physiol.* 47:990–1001 (1979); Klingele et al., (1970), Alveolar shape changes with volume in isolated, air-filled lobes of cat lung, *J. Appl. Physiol.* 28:411–414) and of changes in the state of the air-liquid interface (Bachofen et al., (1979), Alterations of mechanical properties and morphology in excised rabbit lungs rinsed with a detergent, *J. Appl. Physiol.* 47:1002–1010; Gil et al. 1972 (cited above)). However, there are limitations inherent in using fixed tissues. These include: restriction to analysis of static circumstances; difficulties in being certain that no changes occur during the various processes which assail tissue between the original physiological condition and its fixed dehydrated sliced and stained state; and the necessity of studying a specimen from a different lobe or animal to obtain each individual physiological datum.

There is therefore a substantial need for new methods of studying the spatial distribution of changes that are too small to be otherwise detectable and yet are important to gas exchange. Such techniques would provide much needed information on the functioning of healthy lung tissue, as well as information on what constitutes abnormal performance of lung tissue that might be associated with a chronic pulmonary pathological condition.

Emphysema is an example of a chronic obstructive pulmonary disease. It is a debilitating disease affecting 1.65 million Americans, half of whom are over age 65, at an annual cost of over $4 billion. The estimated number of patients has increased over 40% since 1982 and chronic obstructive pulmonary disease (COPD) is the fourth-ranking cause of death in the United States (American Lung Association Lung Disease Data, Publication of American Lung Association, 1994). The lung damage is irreversible and current therapy is usually limited, at best, to symptomatic relief. Lung transplantation is being increasingly used for treatment of emphysema, but it is very expensive and limited by the small number of donor lungs available. More recently, lung reduction surgery, especially in elderly patients with severe emphysema, has gained increasing popularity with chest physicians and surgeons.

The distribution of emphysematous lesions can vary widely, and delineating the boundaries between more versus less affected regions is difficult in situ. Compounding the problem is that the bullous lesions that are detectable with current technology are very large in comparison with intrinsic alveolar size and that septal destruction that decreases the normal surface area, by, e.g., a factor of two, is virtually invisible to current measurement techniques. A method is needed to delineate boundaries between healthy and impaired tissues during surgery to maximise the effectiveness of surgical intervention.

SUMMARY OF THE INVENTION

This invention satisfies the above needs by providing a novel method for determining lung structure and function in the living animal. In a preferred embodiment of the invention a method is provided for measuring lung function in a living animal in a preselected region of the lung, that includes the steps of causing light from an external light source to contact a region of the lung; detecting and measuring the scattering of light subsequent to its contact with the region of the lung; and obtaining functional information about the region of the lung from measurements of light scattering.

Functional information about selected regions of the lung in real time include surface area to volume ratio (A/V), pulmonary capillary blood volume density (Vc) and pulmonary oxygen saturation (S). Measurement of multiple parameters involves utilizing multiple different wavelengths of light and obtaining discrete images for each wavelength of light and correlating the data from these images with lung function.

An embodiment of the invention utilizes the functional information obtained from light scattering measurements to determine the status of lung tissue intraoperatively in patients with chronic obstructive pulmonary disorder such as emphysema and to determine regions of impaired lung function.

In a preferred embodiment, a method is provided for regional identification of functional tissue in respiration impaired animal subjects, including the steps of accessing the lungs in subject and causing a light from an external source to contact a region of the lung, detecting the resulting scattering pattern of light over the region of the lung, measuring the spatial variation of the intensity of the scattered light and identifying functional tissue by the measurements.

In a preferred embodiment, a device is provided for measuring regional lung function, where the device includes an optical fiber having a first end coupled to a source of light and a second end from which light emerges, so that the light emerging from the second end of the fiber is suitable for illuminating a region of the lung; the emergent light being diffusely scattered by the lung tissue; a light collection system, for gathering the diffusely scattered light, the system having a spectral separation device suitable for separating a plurality of wavelengths of light for directing the separated wavelengths of light to a camera so as to form an image; and a video system for receiving the image from the camera such that the image can be digitized and information on lung function calculated. The device may further include a computer, where the computer contains a series of algorithms for converting the image into functional parameters of gas exchange.

(B) shows the effect of a low lung volume history and (c) shows the effect on the optical pattern of exposure to a low inspired $O_2$ mixture ($FIO_2=10\%$).

Figure 6:
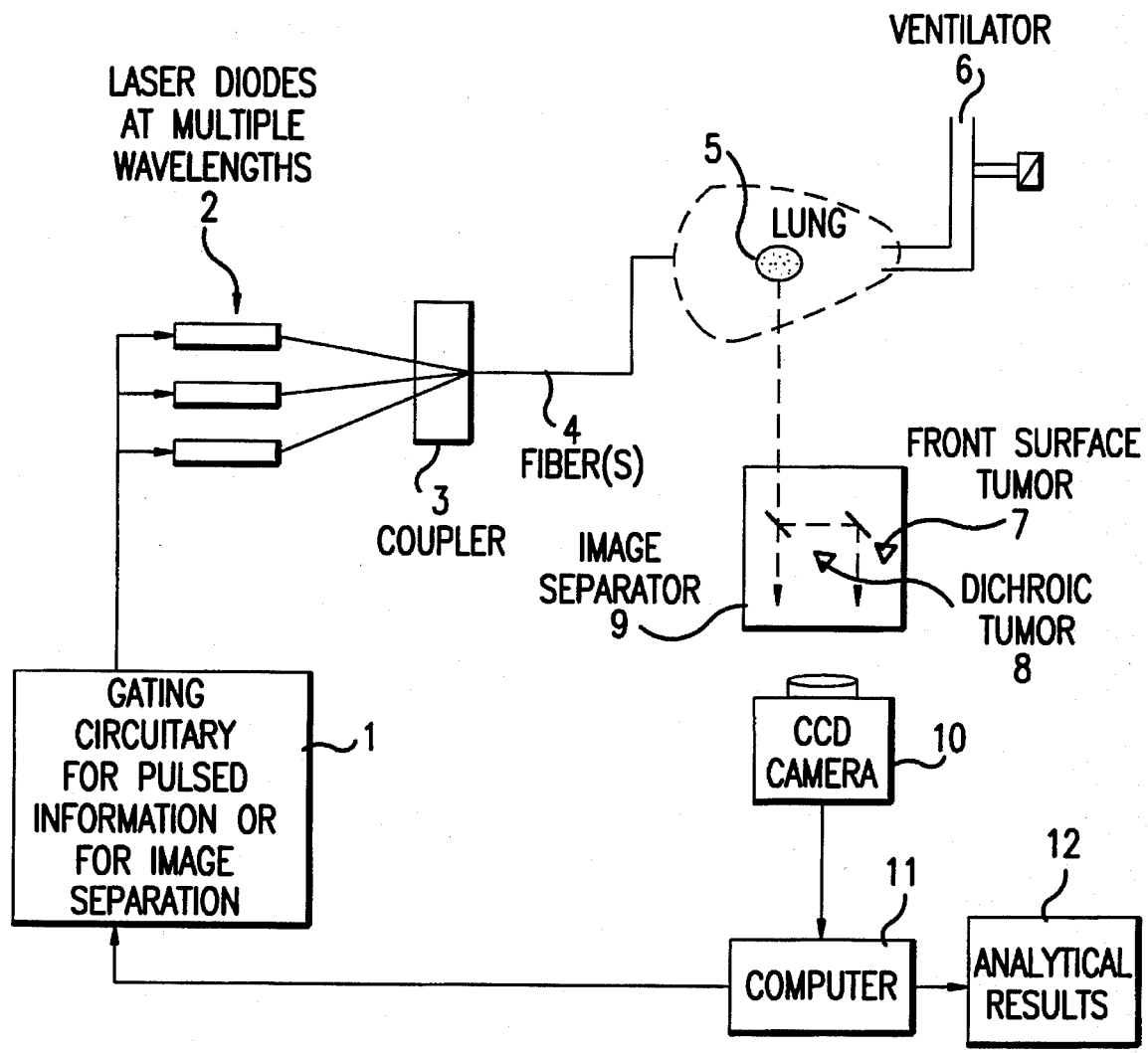

FIG. 6 is the diagrammatic representation of a light collection system to gather the scattered light and separate out the images at the two wavelengths.

DETAILED DESCRIPTION OF SPECIFIC EMBODIMENTS

The present invention is directed to a method and device for measuring functional properties of selected regions of the lung in vivo and in real time.

The term "impaired lung function" is defined here and in the claims to be loss of parenchymal surface and regionally impaired gas exchange.

The term "lung function" is defined here and in the claims as the performance of the lung including its function and dysfunction and including structural properties and/or abnormalities that relate to function.

We have selected rabbits because they have a lung structure and pulmonary vasculature that resembles the human. In addition, rabbits are inexpensive and much of the existing literature is based on work in rabbits.

Optical Properties of the Lung

A glow of light appears on the surface of a lung when it is illuminated by a thin beam of incident light. This backscattered light is the result of multiple scattering in the interior of the lung. The characteristics of such back scattered light constitute a diffuse-scattering problem.

In 1985, Butler et al (J. Appl. Physiol. 58: 89–96) noted that the optical properties of lungs in diffuse scattering are influenced to a large extent by the geometrical properties of the underlying structures. Butler et al. developed a model for relating the optical properties of the lungs to the physiologically interesting geometric parameters of mean alveolar size or mean surface to volume ratio. This theoretical analysis was tested by Suzuki et al (1985) J. Appl. Physiol. 58: 97–104, using excised dog lobes. These in vitro studies were further extended by Butler et al.(1989) J. Appl. Physiol. 67: 1873–1880 who performed dynamic studies on alveolar septa at different times during stress relaxation and recovery. Miki et al. J. Appl Physiol 75: 1630–1636 (1993) extended these observations using rabbits and exploring geometric hysteresis in pulmonary surface to volume ratio (A/V) during tidal breathing in the living animal using laser light at 633 nm.

We have explored for the first time characteristics of lung function in a living animal using scattered light that have been inaccessible by other means. These characteristics including capillary blood volume ($V_c$) and oxygen saturation (S). We have developed a method of obtaining information on several characteristics at essentially the same time by using and interpreting the scattering of individual wavelengths from a beam that contains as many wavelengths of light as characteristics to be studied, the scattering of a single wavelength providing information about a single parameter. We have employed this novel approach to characterize regional lung function and to identify the presence of normal tissue and tissue that has impaired lung function. We have been able to study the functional and structural properties of regions of the lung that are less than 3 centimeters in diameters and may be as small as the diameter of only a few alveoli (a single alveolus has a diameter of ⅓ mm). Commonly we have looked at lung regions sized in the range of 1–2 cm. The significance of this fine resolution can only be properly appreciated in the context of an awareness of the large surface area presented by the entire lung consisting of between 50 and 100 sq meters. Mathematics have been developed to correlate the extent of light scatter at a given wavelength with surface area to volume ratio (A/V), $V_c$ and S. Examples 1 and 2 provide more detailed information concerning experiments utilizing this novel approach.

This approach provides for the first time, the means to obtain multiple readings in fraction of a second time intervals compared with alternative methods that provide mean values over extended periods of time (minutes to hours). Furthermore, it provides a source of real time information on selected regions of the lung which has numerous applications. For example, during an operation a surgeon may wish to know the level of impairment of lung tissue when operating on a patient with emphysema. Other applications of this methodology include the measurement of hemoglobins that have become complexed to molecules other than oxygen such as occurs in carboxy hemoglobin and methemoglobin. For example, patients receiving nitric oxide as therapy for lung disorders form methemoglobin. The ability to measure relative amounts of methemoglobin would provide a measure of the effectiveness of the nitric oxide treatment at its target site in the lung. Other applications of the methodology here claimed is as a measure of heart function. The heart and the lungs are interrelated as the heart sends pulses of blood through the pulmonary capillaries of the lung. Malfunctioning of the heart may be reflected by changes in lung function as could malfunctioning in the lungs result in observable changes in heart function. Yet another application of this approach is to determine the interface between functional and dysfunctional lung tissue surrounding a tumor.

The methodology that we have developed depends on (a) using multiple wavelengths of illumination (b) image seperation at acquisition (c) use of characteristic diffuse scattering. We utilize to our advantage the very properties that have until know made the lung the most problemmatic organ in the body to study. Optically, the lung is very different from all other organs in the body (Suzuki et al. Light scattering by lungs correlates with stereological measurements, *J. Appl. Physiol.* 58(1):97–104 (1985)), because the dominant optical event in the lung is scattering at the septal air-liquid interface due to the very large change in the index of refraction there. This leads to diffuse scattering, and Beer's Law does not apply. Thus, spectrophotometric techniques appropriate to other tissue (see, e.g., Chance, Optical Method, *Annu. Rev. Biophys. Biophys. Chem.* 20:1–28 (1991)) must be greatly modified to study the lung. Nevertheless, exponential extinction still occurs, but the apparent, or diffuse, extinction coefficient $k_{diff}$ bears a different relationship to the concentrations of Hemoglobin (Hb) and oxyhemoglobin (HbO$_2$).

The diffuse optical properties of the lung are conveniently characterized by two parameters, the optical mean free path $L_{opt}$ and the diffuse extinction coefficient $k_{diff}$ (Morse et al., *Methods of Theoretical Physics, Part I.* McGraw-Hill, New York, 1953.). These are given by $L_{opt}=NQ_{tot}/V$ and $k_{diff}^2=(1/L_{opt})^2 3Q_a/Q_{tot}$, respectively, where $Q_{tot}$ is the total optical cross section per septum for scattering, $Q_a$ is the absorption cross section ($Q_a/Q_{tot}$ is the probability of absorption conditional on a photon hitting a septum), and N/V is the number of alveolar septa per unit volume. In terms of more usual quantities, $L_{opt}$ is the optical equivalent of the morphometric mean linear intercept $L_m$, which is inversely related to the surface area to volume ratio A/V (Weibel, Stereological Methods Vol. 1, *Practical Methods for Biological Morphometry*, Chapter 2, Academic Press, London, 1979). (To the degree that alveolar septal are largely transparent $L_{opt}$ is $>L_m$.) The diffuse extinction coefficient $k_{diff}$ reduces, in the absence of elastic scattering, to the familiar Beer's Law extinction coefficient. In the special case of homogeneous unidirectional illumination, the intensity I re-emitted from the pleural surface is approximately $I=I_0 e^{-k_{diff}L_{opt}}$, where $I_0$ is the uniform incident intensity. By contrast, with point illumination, the backscattered intensity I(r), at distance $r>>L_{opt}$, from the source, falls off rapidly as $I(r)=(const)P_O (L_{opt}/r^3)exp-k_{diff}r$, where Po is the incident power and (const) represents geometrical factors associated with the transition to large r (Butler et al., A theory of diffuse light scattering by lungs, *J. Appl. Physiol.* 58(1):89–96 (1985); Butler et al., Step response of lung surface-to-volume ratio by light scattering stereology, *J. Appl. Physiol.* 67(5): 1873–1880 (1989)). It follows that $Ln\ Ir^3=(const)+LnL_{opt}-k_{diff}r$. The negative of the slope of $lnIr^3$ is thus a simple and direct measure of $k_{diff}$, and that fractional changes in the intensity intercept correspond to fractional changes in $L_{opt}$ (i.e., $\delta L_{opt}/L_{opt}=\delta Ln\ L_{opt}$). Further, from changes in $k_{diff}$ at the two wavelengths, changes in S and fractional changes in $V_c$ can be estimated. This follows from the fact that at 805 nm, the absorption of Hb and HbO$_2$ are identical (isobestic), while at 650 nm, the absorption of reduced Hb is almost 10 times higher than for HbO$_2$ (van Assendelft, *Spectrophotometry of Haemoglobin Derivatives*, Charles C. Thomas, Assen, The Netherlands (1970)).

Multiple Wavelengths of Illumination

We have independently estimated changes in mean surface to volume ratio, local capillary blood volume, and state of oxygenation by measuring $k_{diff}$ and the intensity intercept at multiple wavelengths. In an embodiment of the invention, we selected adequate light sources at the two wavelengths chosen to optimize our ability to distinguish heterogeneities in pulmonary capillary blood volume distribution, mean capillary saturation, and surface to volume ratio. Specifically, light with a wavelength of 805 nm is isobestic (equal absorption coefficients) for both reduced and oxygenated hemoglobin, and is used primarily for determination of blood volume distributions. Light of 650 nm wavelength is chosen to accentuate the resolving power of this technique with respect to the heterogeneous distribution of oxygen saturation (van Assendelft 1970, Chance 1991). At that wavelength, the extinction coefficient for reduced Hb is about ten times that of oxygenated Hb. At both 650 nm and 805 nm, the absolute value of the absorptions is neither too low, which would compromise the signal to noise ratio insofar as the absorptive characteristics of the lung would be dominated by the non-blood tissue component, nor is too high, which would imply that only little light would be backscattered, thus requiring commensurately high power optical sources.

The light sources at these wavelengths can be laser diodes (FIG. 6 (2)) although other light sources may be used. The power of the light source should be sufficiently high (for example; 50 mW) to be able to effectively photograph the pleural surface of lungs, but sufficiently low that there is no danger of heating the lung tissue. To study the effects of illumination by two wavelegths, two diodes are coupled (3) through optical fiber couplers to a single fiber (4), which is then used to either diffusely illuminate the lung's pleural surface in flood mode illumination by holding the source fiber 5 to 10 cm away from the surface, or to provide point mode illumination by placing the fiber on the pleural surface (5). This form of illumination is used in anesthetized, thoracotomized animals (see below). In an embodiment of the invention(also see example 1) the sources are electronically gated (1) to provide pulses of approximately 10 msec duration, triggered by a pre-selected phase in either the cardiac or respiratory cycle. This pulse width is chosen to satisfy two requirements. First, it must be sufficiently short that physiological changes associated with, e.g., the cardiac cycle do not compromise the optical pattern. Second, it must be sufficiently long that the energy delivered per pixel to the CCD camera (10) is adequately high. We estimate that total energy input to the lung in Example 1 of 500 µJ is sufficient to obtain useful measurements of diffuse scattering. Verification of fiber optic output can be determined using a fast response radiometer.

Image Separation and Acquisition

A light collection system gathers the scattered light and separates out the images at each of the wavelengths (see image separator (9)). In an embodiment of the invention, two wavelengths are separated using a spectral separation device such as a dichroic mirror (8), which provides for good separation of wavelengths with little loss in intensity. (see FIG. 6). It is also possible in other embodiments to substitute a mirror for a prism or other devices capable of separating spectra. The dichroic beam splitters are designed to have a high reflectivity at the 805 nm wavelength and high transmission at the 650 nm wavelength. They are made by depositing layers of dielectric coating materials onto a glass substrate. These layers provide the wavelength selective reflection and transmission characteristics noted above and can be tested with available conventional light sources. The two beams, split in a wavelength dependent fashion by the dichroic mirror, are directed into a CCD camera. This optical system consists of several mirrors on adjustable mounts to separate and recombine the images appropriately. The size and location of the two images in the CCD allows for simultaneous viewing by the video system. Each video frame can then be digitized and the information at both wavelengths extracted. Although a description is provided here for image separation of diffuse scattering from two wavelengths, the method is not limited to two wavelengths but rather can also be used for 3 or more wavelengths as desired using appropriately selected mirrors to separate the images.

Use of Data Provided by Images of Diffuse Scattering

The images at the multiple wavelengths are stored digitally (11) and analyzed both for changes in $k_{diff}$ and $L_{opt}$ in the point illumination mode and for fractional deviations of the intensity pattern in the flood mode. In an embodiment of the invention, the data obtained from analyzing diffuse scattering from two wavelengths is used to construct regional maps of changes in $L_{opt}$ and changes in S and $V_c$ as functions of an orthogonal reference grid on the pleural surface. An additional map of specific ventilation V may be constructed from the displacement of markers on the pleural surface. The four regional maps $\delta L_{opt}/L_{opt}$, v, S, and $V_c$, can be quantitatively analyzed in two distinct ways. First, autocorrelation analysis is performed on each map separately. The characteristic distances revealed by the falloff in autocorrelation will be used to quantify regional variability. Second, cross-correlation analysis is performed on each of the pairs of maps. Other parameters of lung structure and function can be analyzed similarly.

To facilitate the interpretation of the images, computer programs which include algorithms to subtract background from signal; identify the optical center of the light in the image, indentify the defuse regime; and register dual images to form a single image.

EXAMPLES

Example 1: The Measurement of Fluctuations of $V_c$ and S During the Cardiac Cycle Using Diffuse Optical Scattering in Healthy Lung in Vivo Four New Zealand White rabbits were anesthetized, tracheotomized, and ventilated. Anesthesia in the rabbits was induced with ketamine 30–50 mg/kg+xylazine 1–2 mg/kg im. The level of anesthesia was continuously assessed by pulse rate, blood pressure, corneal reflex, spontaneous movement, and movement in response to toe (paw) pinch. Maintenance anesthesia was provided as needed with incremental doses of pentobarbital 2–4 mg/kg iv.

After being anesthetized, an intravenous line was placed in the ear for maintenance of anesthesia, an arterial line was also placed in the ear or carotid, tracheotomy was performed and the institution of mechanical ventilation (tidal volume 10 ml/kg at 30–50 breaths/min.)was initiated. A thoracotomy was performed on the left side, exposing a region of the lung's pleural surface about 1×3 cm.. Monitoring included arterial oxygen saturation via a pulse oximeter- ($SpO_2$) on the tongue, BP, ECG. Positive end expiratory pressure (PEEP) was maintained at 3 cm $H_2O$, with ventilation sufficient for $SpO_2 > 90\%$.

Point Illumination

Following our technique described elsewhere and incorporated here by reference (Miki et al. Geometric hysteresis in pulmonary surface-to-volume ratio during tidal breathing. *J. Appl. Physiol.* 75(4):1630–1636 (1993)), a point-like source of light was introduced at the pleural surface through an optical fiber mounted in a tuberculin stopper and placed on the pleural surface. The light source was a tunable pulsed dye laser, which allowed us to investigate the optical characteristics at 650 nm and at the approximately isobestic point of 800 nm. The pattern of backscattered light from the pleural surface (a roughly 2 cm diameter "glow") was photographed by a charge coupled device (CCD) camera, whose shutter was triggered to capture the image from one laser pulse.

Figure 1:
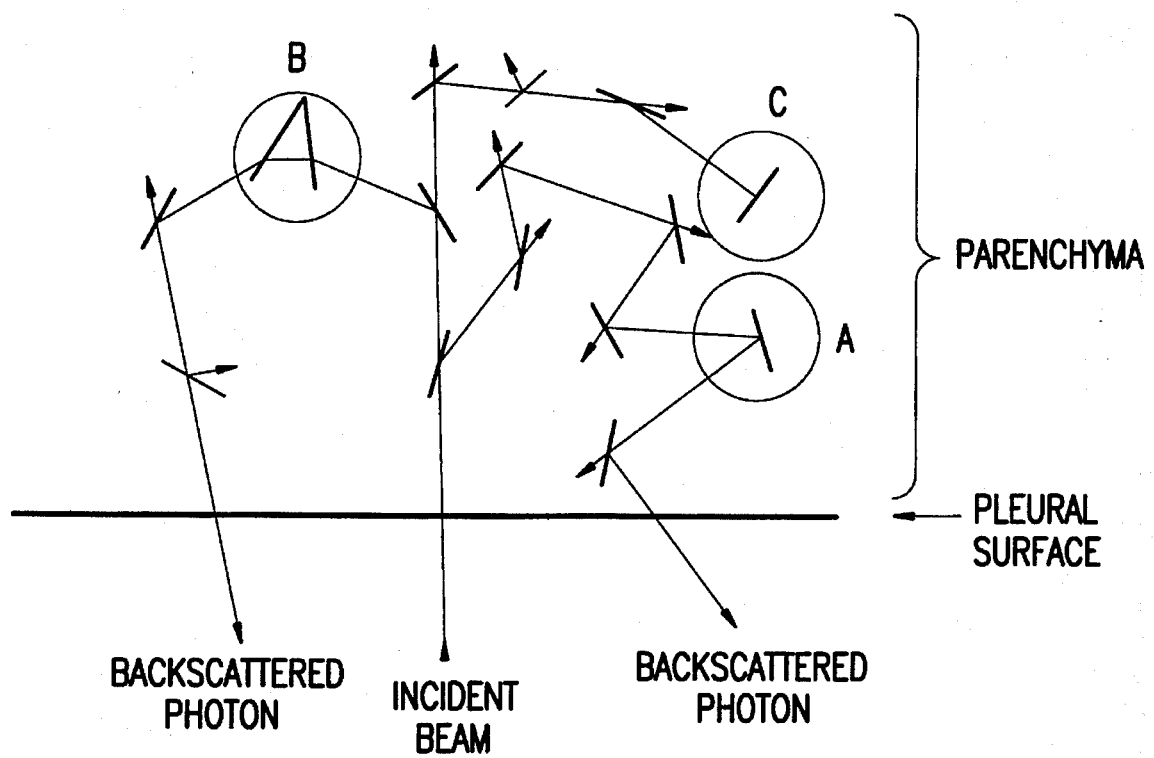
FIG. 1 is a diagram of several possible photon paths in parenchyma. A, reflective scattering event; B, refractive event; C, absorptive event.
Figure 2:
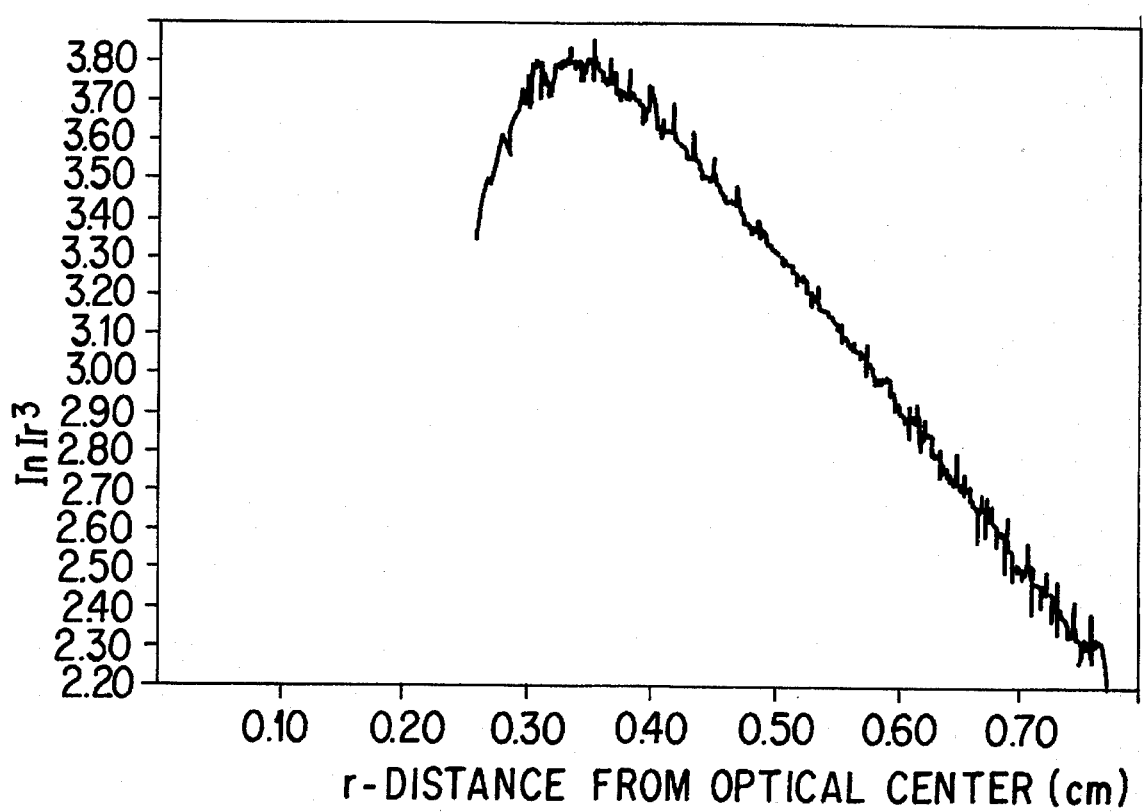
FIG. 2 is a typical graph from a single photograph taken at transpulmonary pressure (Ptp) of 5 cm $H_2O$ and at a wavelength of 800 nm; and demonstrates the fall off of light intensity I emitted from the pleural surface with the distance r from a point light source in a manner such that $\ln(Ir^2)$ is approximately linear in r.

Following a period of normal ventilation, the lungs were held at a Ptp of 5, 10, or 15 cm $H_2O$, at which a sequence of photographs were taken over a period of a few seconds, without synchrony between the picture frequency and the heart beat. This protocol was repeated at both wavelengths. As remarked above, in the diffuse scattering regime, the light intensity I emitted from the pleural surface falls off with the distance r from a point light source in a manner such that $\ln(Ir^3)$ is approximately linear in r (Butler 1989). FIG. 2 shows a typical graph of this function, from a single photograph, taken at a Ptp of 5 cm $H_2O$ and at a wavelength of 800 nm. Note that for r greater than about 0.35 cm, the data are strikingly linear, indicating the onset of diffuse scattering and the appropriateness of our analysis.

Figure 3:
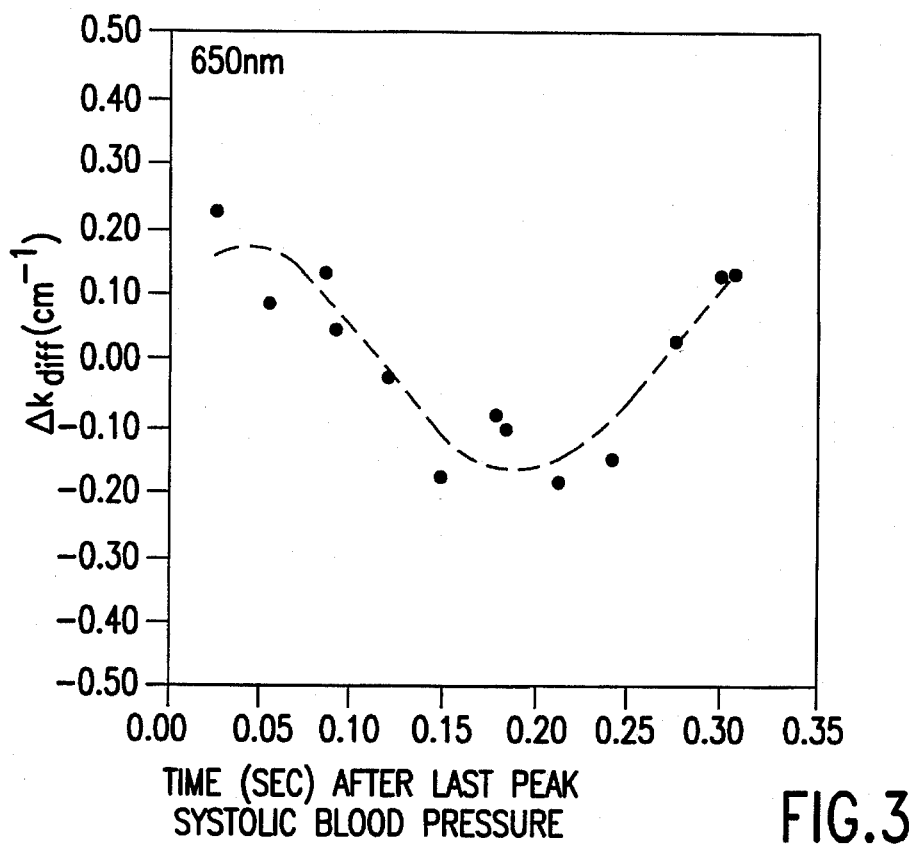
FIG. 3 shows how $k_{diff}$ changes at 650 nm over the heart beat in a New Zealand White rabbit at Ptp=5 cm $H_2O$, where the fluctuations are significant ($p<0.05$ by analysis of variance).
Figure 4:
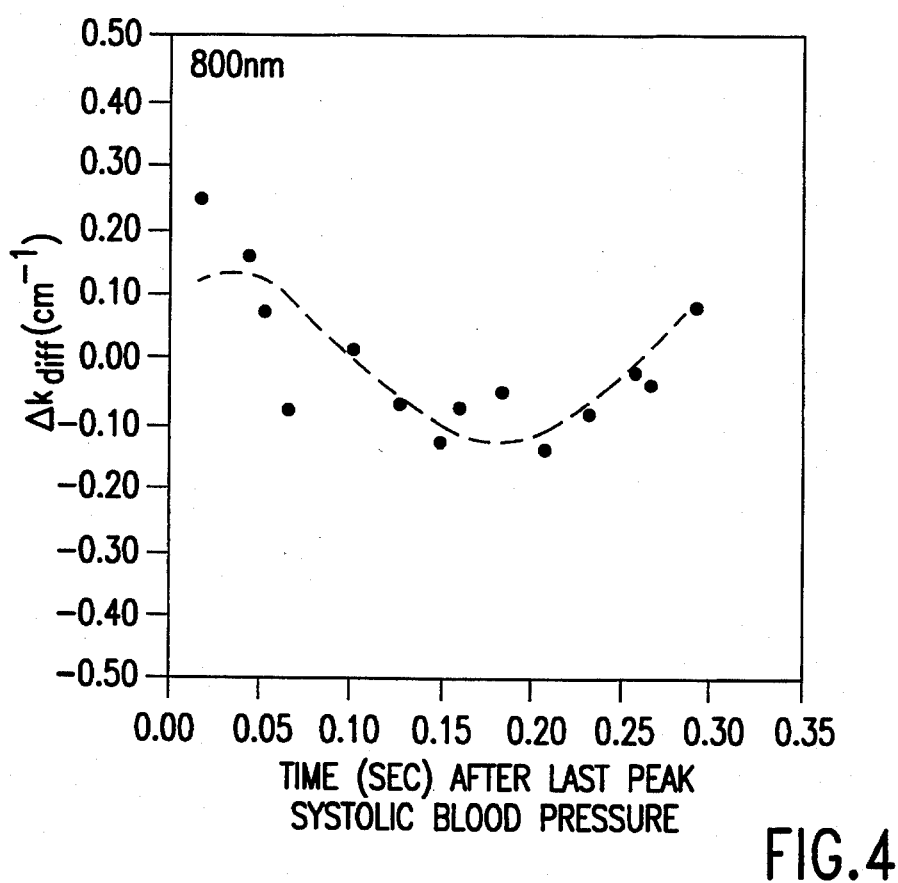
FIG. 4 shows how $k_{diff}$ changes at 800 nm over the heart beat in a New Zealand White rabbit at Ptp=5 cm $H_2O$, where the fluctuations are significant ($p<0.05$ by analysis of variance).

The diffuse extinction coefficient $k_{diff}$ can be directly measured from the $\ln(Ir^3)$ plot in the far field and is an indication of the absorption probability. At a fixed lung volume, where $L_{opt}$ is constant, $k_{diff}$ depends only upon $V_c$ at 800 nm and on both $V_c$ and S at 650 nm. We found that $k_{diff}$ fluctuates phasic with the cardiac cycle by Fourier analysis of the time dependence of the measured $k_{diff}$. FIGS. 3 and 4 above show how $k_{diff}$ changes at 650 nm and 800 nm over the heart beat. Both are at Ptp=5 cm $H_2O$, and the fluctuations are significant (p<0.05 by analysis of variance). The fractional change in $V_c$ was about 10% and mean S was about 80% but with negligible variation. At higher PTP, however, the fractional change in Vc decreased while changes in S became significant also reaching levels of 10%. These fluctuations lagged behind peak systemic blood pressure by ⅛ cycle. These results are consistent with fluctuations in pulmonary capillary pressure and gas exchange over the cardiac cycle and with decreasing capillary compliance with increasing PTP.

Flood Illumination

Figure 5A:
FIGS. 5A–C are isointensity images of backscattered light pattern at 650 nm from a rabbit in different physiologic conditions, where the isointensity contours are shown in false gray scale, each gray level representing from the center position outward a different and gradually decreasing intensity level. (A) shows a smoothly varying intensity pattern, maximal at the center where the pleura is normal to the illuminating fiber, and falling off with the lung's curvature.
Figure 5B:
Figure 5C:
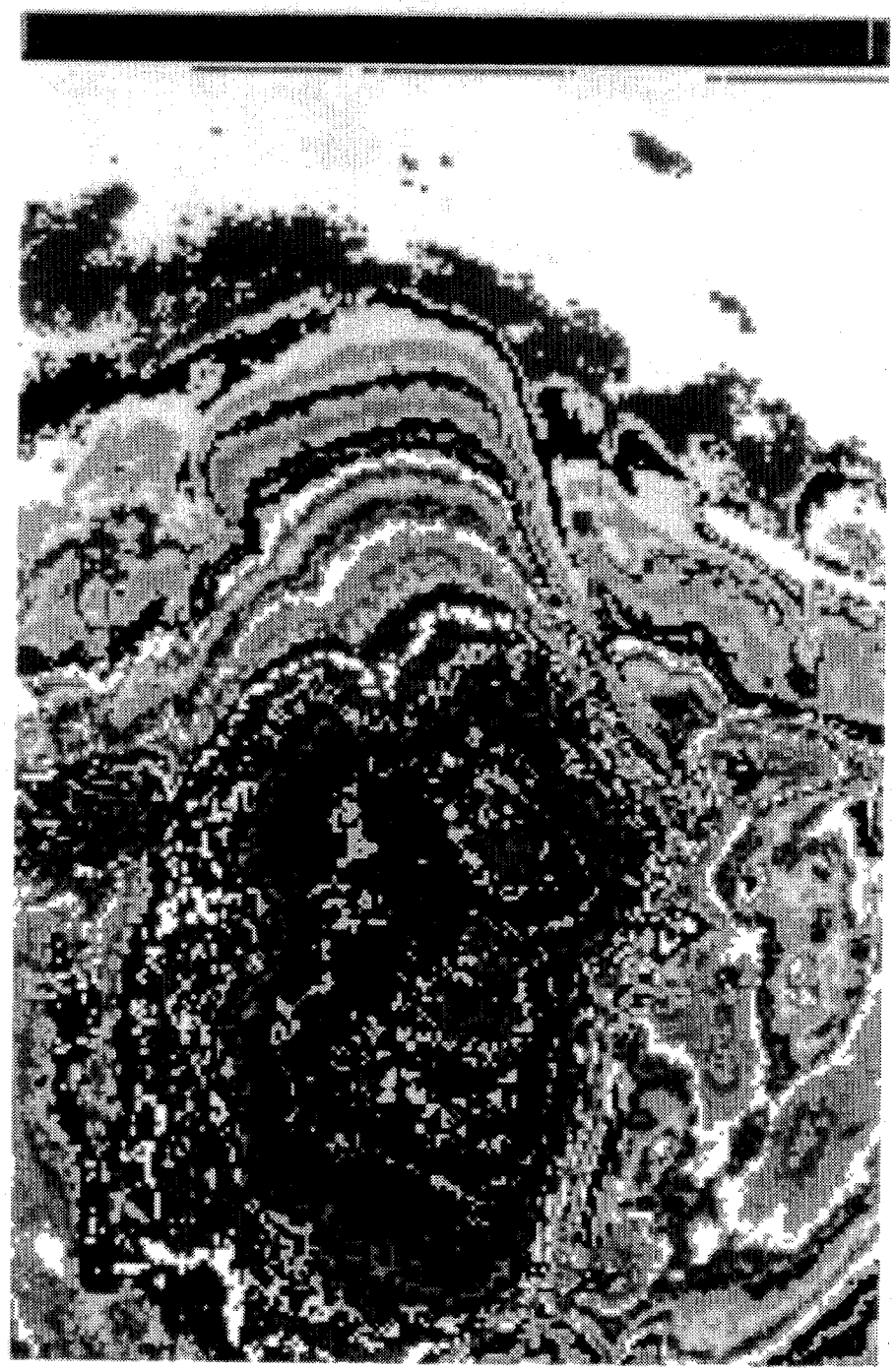

We illuminated the pleural surface in the same thoracotomized rabbit preparation as described above by holding the source optical fiber approximately 5 cm away from the pleural surface. The acceptance and emission angle of the fiber was such as to provide smoothly varying illumination over the field of view. Due to the large intrinsic curvature of the rabbit lung, however, the functional illumination was maximal where the surface was normal to the illuminating fiber axis, and dropped off systematically with the lung's curvature. FIGS. 5A–C show isointensity images of the backscattered light pattern at 650 nm from one animal in different physiologic conditions. The isointensity contours are shown in false gray scale, each gray level representing, from the center position outward, a different and gradually decreasing intensity level. FIGS. 5A–C were taken of the same lung region, at an end expiratory pressure of 3 cm $H_2O$. FIG. 5A shows a smoothly varying intensity pattern, maximal at the center where the pleura is normal to the illuminating fiber, and falling off with the lung's curvature. This figure represents the "uniform" baseline image, departures from which indicate regional variations in surface to volume ratio, capillary blood volume, and oxygen saturation.

FIG. 5B shows the effect of a low lung volume history. The lung was allowed to deflate to minimal volume (a Ptp of zero) for several seconds in order to induce regions of atelectasis The lung was subsequently ventilated with standard PEEP for 1 min and normal tidal volume, but with no intervening sighs or deep breaths. The heterogeneous character as inferred by departures of the isointensity map from the control state is marked. While it is no surprise that atelectasis should accompany deflation to zero pressure, the picture shown here displays the heterogeneous character of the subsequent reinflation from that state. Later pictures taken following continued normal ventilation with occasional deep breaths to total lung capacity (TLC), defined by a Ptp of 30 cm $H_2O$, showed continual recovery, but our technique could discern substantial and persistent residual inhomogeneities long after the expected time for complete recovery.

FIG. 5C shows the effect on the optical pattern of exposure to a low inspired $O_2$ mixture ($FIO_2$=10%) ($FIO_2$ is the fraction of oxygen in inspired gas). This is a remarkable picture, as the lung had had no ventilatory insults, and its baseline behavior was similar to the control picture above. Since this picture was taken at 650 nm, and the only experimental intervention was to lower the $FIO_2$, the resulting inhomogeneous character can only be explained by a combination of regional variability in oxygen saturation coupled with, perhaps, variation in capillary blood volume secondary to heterogeneous hypoxic vasoconstriction. This is a surprising result, because it is generally thought that the normal lung is relatively homogeneous in its structural and gas exchange properties and in its response to low oxygen levels. Our technique demonstrates that the lung displays a regionally disparate response in gas exchange with low $FIO_2$ insults. This striking result may be caused primarily to gas exchange inhomogeneities exacerbated by the low $FIO_2$ or is secondary to a primary heterogeneity in hypoxic vasoconstriction. Resolution of this ambiguity can be determined by correlating the observed phenomenon with pictures at 805 nm. The use of diode lasers can provide sufficient power at multiple wavelengths to examine this effect and thereby allow us to quantitatively evaluate the physiologic effect of low $FIO_2$ in terms of its effect on $V_c$ and S. We have selected the power of the light source to maximise the light reaching the pleural surface while not heating the lung tissue thereby avoiding any damage that might arise from this source.

Example 2: Independent Estimation of Changes in Mean Surface to Volume Ratio, Local Capillary Blood Volume Density and State of Oxygenation Ten live female New Zealand rabbits, (3–4 kg) are anesthetized, ventilated, and thoracotomized as described in Example 1. The lung was illuminated by flood and point illumination as described above and both flood and point source pictures are taken a. Measuring changes in lung mechanics. To test our ability to measure changes in lung geometry and secondary gas exchange abnormalities, we expose animals to low lung volume histories which lead to a spatially variable pattern of atelectasis and mean capillary oxygen saturation that is regionally correlated with the mechanical abnormalities. The mechanical heterogeneity in specific ventilation is compared with optical estimates of A/V. Gas exchange heterogeneity is determined by optical estimates of $V_c$ and S.

Baseline optical and specific pleural displacement measurements are performed through a wide thoracotomy. The lungs are allowed to collapse to positive end expiratory pressures ranging from 0 to the baseline PEEP, for periods of up to 10 sec to allow for airway closure. Optical measurements are then taken. The animals are ventilated with both normal and low tidal volumes, with frequency adjusted to maintain adequate ventilation as assessed by an end tidal PCO2 of ~40 torr, but without large pressure swings to reopen the airways. Optical and specific ventilation measurements are repeated. Following these maneuvers, the lungs are expanded to transpulmonary pressures of 25–30 cm $H_2O$ to expand closed units. Mechanical ventilation is reinstated at the previous levels of PEEP. The saturation, blood volume, and specific ventilation maps is then compared from baseline to the collapsed, low PEEP ventilated state, and following multiple deep breaths again to the low PEEP ventilated state. Changes in specific ventilation patterns are interpreted as reflecting airway closure; subsequent changes back toward baseline are interpreted as reopening of closed units. Changes in the saturation map are used to infer the gas exchange consequences of airway closure, and the ventilatory and saturation maps are compared and correlated to obtain a determination of A/V.

b. Measuring changes in gas exchange. To determine changes in oxygen saturation of pulmonary capillary blood in the absence of mechanical changes, we expose animals to hypoxia induced by ventilation with low inspired oxygen mixtures.

Independent semi-quantitative assessment of changes in mean saturation are performed on rabbits made hypoxic by ventilation with low inspired oxygen fractions such that arterial blood saturation will fall to 50%. $SpO_2$ is continuously monitored. Mixed venous blood saturation is here assumed to drop linearly with $SpO_2$ to the extent that $VO_2$ and cardiac output remain constant. The saturation of capillary blood with diffuse scattering is quantified by correlating $SpO_2$ with optically determined S from sequential changes in $k_{diff}$ at 650 nm (corrected for blood volume changes assessed by changes in $k_{diff}$ at 805 nm).

Observations are made at both wavelengths in open chested hypoxic rabbits, and optical estimates of S are compared with arterial saturation measured oximetrically. For each of the above physiological protocols, baseline $k_{diff}$'s is measured at both 650 nm and 805 nm at various points on the pleural surface followed by measurements of regional backscattered intensity patterns with uniform illumination. The ratio of the backscattered intensity to the incident intensity in such a case is approximately given by $\exp(-k_{diff}L_{opt})$, and so, using the measurements of $k_{diff}$ with point illumination as fiducial markers, a regional map of $k_{diff}$ is constructed. Independent variations in $L_{opt}$ are assessed by fractional changes in the overall intensity pattern, as described above. These baseline studies are conducted over the cardiac and respiratory cycles to establish the effect of these independent variations. Differences in the regional variations of $k_{diff}$ are used as a quantitative representation of the regional variability in Vc and S.

Animals are ventilated with a range of inspired oxygen fractions ranging from 11% to 21% to assess the contribution of hypoxic pulmonary vasoconstriction (HPV) to alterations in gas exchange and to subsequet resolution dependency on volume history. Both flood and point optical measurements are made at FRC for each $FIO_2$. Exposure to low $FIO_2$ causes marked changes in S, minimal changes in $\delta L_{opt}/L_{opt}$, and a high correlation between the heterogeneity in S and that of $V_c$ to the extent that the hypoxic pulmonary vasoconstrictive response (HPV) is uniformly dose dependent on local $PO_2$. The time course of resolution of the heterogeneous response to low $FIO_2$ following return to ventilation with room air is monitored and regional s and $V_c$ are correlated together with correlation of changes in S with arterial saturation.

Regional Specific Ventilation Measurements

To measure the regional variability in specific ventilation v, the displacement of pleural markers is used (Lehr et al., Photographic measurement of pleural surface motion during lung oscillation, *J. Appl. Physiol.: Respirat. Environ. Exercise Physiol.* 59:623–633 (1985), incorporated here by reference). Ink dots are placed on the pleura in a lattice pattern, with 1 cm spacing. The displacement of the individual dots is measured by the pixel displacement in the CCD image of corresponding dots from their positions at end expiration and end inspiration. For each 1×1 cm² square, the fractional change in area $\Delta A/A$ between FRC and FRC+VT is computed. Regional specific ventilation is estimated by assuming approximate geometric similarity in the dimension perpendicular to the pleural surface, for which $v=\Delta V/V=1.5 \Delta A/A$ at that lattice position.

We correlate the changes in $k_{diff}$ seen with changes in blood volume by optically mimicking changes in $V_c$. Indocyanine green dye (ICG) was developed for a desirable optical absorption peak at 805 nm, the isobestic point for Hb and $HbO_2$, and represents an optical $V_c$ mimic. Thus, since the absorption probability $Q_d/Q_{tot}$ is given by a sum over absorbing species, we find at a fixed lung volume that the contribution from blood to $k_{diff}^2$ at the isobestic wavelength of 805 nm is $\epsilon_{Hb}[Hb]V_c+\epsilon_{ICG}[ICG](1-HCt)V_c$, where $\epsilon_{Hb}$, $\epsilon_{ICG}$, [Hb] and [ICG] are the raw extinction coefficients and concentrations of Hb and ICG, and Hct is the hematocrit. It follows that, for known $\epsilon$'s (van Assendelft 1970), measurable variations in $k_{diff}^2$ with changes in [ICG] determined photometrically suffice to calibrate the relationship between measured changes in $k_{diff}^2$ and changes in $V_c$. This calibration is systematically determined as a function of lung volume by repeating the measurements at selected Ptp's covering the vital capacity.

Although certain preferred embodiments of the present invention have been described, the spirit and scope of the invention is by no means restricted to what is described above.

We claim:

1. A method for measuring lung function in a living animal subject comprising;
   (a) causing light of at least one wavelength, to contact a region of the lung within the subject; wherein the at least one wavelength includes an isobestic wavelength;
   (b) detecting a diffuse scattering pattern of light of each wavelength subsequent to its contact with the lung region;
   (c) measuring the diffuse scattering pattern detected in step (b) to provide scattering data and;
   (d) determining lung function information from the scattering data.

2. A method according to claim 1, wherein step (a) further comprises selecting a plurality of wavelengths for contacting the region of the lung and causing each wavelength of light to emerge from a separate external light source.

3. A method according to claim 2, comprising selecting light having wavelengths of 650 nm and 805 nm for contacting a preselected region of the lung.

4. A method according to claim 3, comprising detecting the scattering of the two wavelengths and obtaining two discrete light scattering images.

5. A method according to claim 4, comprising measuring the scattered light and obtaining functional information about at least one property selected from the group consisting of pulmonary capillary blood volume (Vc) and pulmonary oxygen saturation (S) at the preselected region of the lung.

6. A method according to claim 4, comprising measuring the scattered light and obtaining functional information about at least two properties selected from the group consisting of surface area to volume ratio (S/A), pulmonary capillary blood volume (Vc) and pulmonary oxygen saturation (S) at the preselected region of the lung.

7. A method according to claim 1, further comprising: performing steps (a) through (c) for each of a first region and a second region and using scattering data provided in step (c) for each region to provide a comparison of lung function information of the first region of the lung with that of the second region.

8. A method according to claim 7, further comprising step (d) of identifying regions of impaired lung function.

9. A method according to claim 8, wherein the animal is a human subject and where the subject is suffering from chronic obstructive pulmonary disease.

10. A method according to claim 8, wherein the animal is a human subject and where the subject is suffering from respiratory distress syndrome.

11. A method according to claim 8, wherein the animal is a human subject and where the subject is suffering from cardiac malfunctioning.

12. A method according to claim 7, further comprising correlating measures of light scattering to determine the effect of any atypical hemoglobin in the lungs formed after exposure to external agents.

13. A method according to claim 1, wherein step (a) further comprises causing light from an external light source to contact a region of the lung during an invasive procedure.

14. A method according to claim 13, wherein the invasive procedure is selected from the group of surgical methods consisting of open chest surgery and thoracoscopy.

15. A method according to claim 13, wherein the invasive means is bronchoscopy.

16. A method according to claim 1, wherein step (a) further comprises causing light from an external light source to contact a region of the lung by non-invasive means.

17. A method according to claim 16, wherein the non-invasive means comprises directing a light through the intercostal spaces of the chest wall.

18. A method according to claim 1, wherein step (a) of causing light to contact a region of the lung further comprises providing illumination of the type selected from the group consisting of point and flood illumination.

19. A method according to claim 1, wherein step (a) of causing light to contact a region of the lung further comprises providing flood illumination followed by point illumination.

20. A method according to claim 1, wherein the scattering data in step (c) further comprises measuring the absorptive scattering by the diffuse extinction coefficient at multiple wavelengths, and fractional changes in the optical mean free path.

21. A method for regional identification of functional tissue in a respiration impaired animal subject, comprising;

(a) accessing the lungs in the subject and causing a light of at least one wavelength to contact a region of the lung within the subject; wherein the at least one wavelength includes an isobestic wavelength;

(b) detecting a diffuse scattering pattern of light over the region of the lung;

(c) measuring the spatial variation of the intensity of the scattered light detected in step (b);

(d) identifying functional tissue by the measurements obtained in step (c).

* * * * *